(12) United States Patent
Kita et al.

(10) Patent No.: US 7,140,230 B2
(45) Date of Patent: Nov. 28, 2006

(54) ODOR MEASURING APPARATUS

(75) Inventors: Jun-ichi Kita, Kyoto-fu (JP); Kunihiko Ohkubo, Shiga-ken (JP)

(73) Assignee: Shimadzu Corporation, Kyoto (JP)

( * ) Notice: Subject to any disclaimer, the term of this patent is extended or adjusted under 35 U.S.C. 154(b) by 114 days.

(21) Appl. No.: 11/093,263

(22) Filed: Mar. 30, 2005

(65) Prior Publication Data
US 2005/0252275 A1 Nov. 17, 2005

(30) Foreign Application Priority Data
Mar. 31, 2004 (JP) .............................. 2004-102524

(51) Int. Cl.
*G01N 7/00* (2006.01)
(52) U.S. Cl. ................... 73/23.34; 73/23.2; 73/23.41; 73/31.06
(58) Field of Classification Search ............... 73/23.34, 73/23.2, 23.41, 31.06, 31.07
See application file for complete search history.

(56) References Cited

U.S. PATENT DOCUMENTS

| 4,888,295 | A | 12/1989 | Zaromb et al. | |
|---|---|---|---|---|
| 6,494,077 | B1 * | 12/2002 | Aoyama et al. | 73/23.34 |
| 6,834,530 | B1 * | 12/2004 | Kita et al. | 73/23.34 |
| 2003/0022082 | A1 | 1/2003 | Ohmura et al. | |

FOREIGN PATENT DOCUMENTS

| EP | 1 336 844 A2 | 8/2003 |
|---|---|---|
| JP | 2003-315298 | 11/2003 |
| WO | PCT 99/61902 | 12/1999 |

OTHER PUBLICATIONS

Shimadzu, Solutions for Science, Analytical Instruments, Fragrance & Flavor Analyzer, (2-pages).
Gerstel, Global Analytical, Gerstelus.com, GC Autosampler, Multidimensional GC, off odor analysis (3-pages).

* cited by examiner

*Primary Examiner*—Hezron Williams
*Assistant Examiner*—Rodney Frank
(74) *Attorney, Agent, or Firm*—Westerman, Hattori, Daniels & Adrian, LLP.

(57) ABSTRACT

The present invention provides an odor measuring apparatus capable of assuredly detecting and evaluating such odors that cannot be detected by a measurement apparatus using conventional odor sensors. In an embodiment of the present invention, a gas sample to be measured is introduced into the column 10 of a gas chromatograph 1 to temporally separate it into odor components, which are then introduced into a mass spectrometer (MS) 2 and an odor discriminator 3 in parallel. The data processor 51 creates a chromatogram and/or a mass spectrum from the detection signals generated by the detector 24 of the MS 2, and also calculates the similarity of each odor component to standard odors and/or the degree of contribution from the detection signals generated by the detection circuit 33 of the odor discriminator 3. The processor 51 displays a similarity radar chart or similar graphic information on the display 53, where each peak present on the chromatogram is associated with the information. Even if the odor to be measured is a mixed odor, the GC 1 temporally separates it into sample components, and each sample component can be assuredly and objectively detected by the odor discriminator 3.

6 Claims, 3 Drawing Sheets

ODOR MEASURING APPARATUS

The present invention relates to an odor measuring apparatus for qualitatively or quantitatively measuring odors.

BACKGROUND OF THE INVENTION

Conventionally, the discrimination and evaluation of odors is performed by the olfactory sense of human beings. By this method, it must be considered that different persons (or panels) have different olfactory sensitivities and the olfactory sense of a panel may change depending on the physical condition on the day of the test. Therefore, to obtain an objective result with high accuracy, it is necessary to gather an adequate number of panels and to conduct the test under an adequately uniform environmental condition. Thus, the test often consumes a lot of time and labor. Further, even under a desirable physical and environmental condition, it is very difficult to obtain a conclusive result based on a fixed standard because the olfactory sense of the human being easily adapts to odors.

In view of such problems, some conventional methods use a gas chromatograph (GC) or a gas chromatograph/mass spectrometer (GC/MS) to analyze and discriminate the components of the odor concerned. These methods treat the odor as a volatile chemical substance and can effectively identify the causative agent of the odor. However, the conventional methods cannot correlate the odor composition with the organoleptic evaluation by the olfactory sense of the human being.

A conventional device that is designed to make up for the aforementioned problem is a product of Gerstel (http://www.gerstelus.com), called the "Olfactory Detector Port (ODP-2)." ODP-2, which is an attachment for a gas chromatograph, allows a panel to smell the effluent sample separated by the column of the gas chromatograph and enter information about the odor intensity in real-time while the sample is being analyzed with the detector. The information entered by the panel is used to create a graph showing the change of the odor intensity with time. The relation between the chromatogram created by the gas chromatograph and the aforementioned graph enables the analysis on the relation between the odor composition and the organoleptic evaluation. The aforementioned device, however, has a problem in that it requires the panel to continue smelling the odor for a relatively long period of time (for example, one hour). Concentrating on the smelling of the odor for such a long time not only imposes a burden on the panel but also causes the adaptation of the olfactory sense to the odor, as explained previously. Furthermore, the method cannot be used if the odor contains a harmful substance.

A group including an inventor of the present invention has developed an odor discriminating apparatus using odor sensors responsive to odorous substances, as disclosed in the Japanese Unexamined Patent Publication No. 2003-315298 and on the following website: http://www.an.shimadzu.co.jp/products/food/ffl.htm. The apparatus includes plural pieces of odor sensors having different response characteristics and calculates the quality and intensity of an odor by processing the detection signals of the odor sensors by a cluster analysis, a principal component analysis or other types of multivariate analysis, or by a non-linear analysis using neural networks. This type of odor discriminating apparatus treats an odor as a mixed odor and does not separate it into components, enabling the comparison and determination of mixed odors or the calculation of an odor index or other index indicating the odor intensity in terms of the olfactory sense of the human being. This apparatus, however, sometimes fails to detect a very small quantity of an odor component accompanied by a large quantity of another odor component.

Recently, the growing awareness of environmental issues has increased the necessity for odor measurements, and the measurement should now cover a wider variety of odors that have very complex compositions. However, none of the above-described conventional methods can satisfy this requirement. They reflect only a limited aspect of the odor, which may lead to a misunderstanding of the measurement result in some cases. Furthermore, since the measurement result is devoid of objectivity, it is often difficult to compare plural sets of measurement results obtained at different spots and/or different points in time. Another problem is that the measurement efficiency is hard to improve. In view of such problems, the main object of the present invention is to provide an odor measuring apparatus capable of efficiently measuring a mixed odor having a complex composition with a high level of objectivity.

SUMMARY OF THE INVENTION

To solve the above-described problems, the present invention provides an odor measuring apparatus for analyzing a target gas having an odor, which includes:

a) a component separator for temporally separating the target gas into sample components;

b) a detector having m pieces of odor sensors for sequentially detecting the separated sample components with the lapse of time, where m is an integer greater than one and the odor sensors have different response characteristics;

c) a reference data storage for storing data representing n pieces of reference odor vectors or reference odor curves defined by the results of the measurements of n types of known standard odors within an m-dimensional space formed by detection signals of the m pieces of the odor sensors;

d) a calculator for locating, within the m-dimensional space, a measurement point representing the detection outputs generated by the m pieces of the odor sensors at a certain point in time, and for calculating an index indicating the similarity between the sample component detected at the aforementioned point in time and the standard odors and/or an index representing the degree of intensity of the unknown odor on the basis of the positional relation of the measurement point to the n pieces of the reference odor vectors or the reference odor curves stored in the reference data storage; and e) an information creator for creating a piece of information showing the change of the index with the lapse of time.

The component separator is typically a chromatograph having a separation column into which the target gas is introduced as a gas sample. The separation column temporally separates the gas sample into sample components while the gas sample is passing through it. With the lapse of time, the gas sample exits from the separation column and enters the detector. Then, the m pieces of the odor sensors generate detection outputs for each component contained in the gas sample.

According to the present invention, the m pieces of the odor sensors have different response characteristics. Therefore, it is possible to define an m-dimensional space having m pieces of axes corresponding to the detection outputs of the m pieces of the odor sensors, where the origin indicates "no odor." Detection outputs of the odor sensors for a given odor can be located as a measurement point within the m-dimensional space. If the odor intensity increases, the measurement point moves away from the origin. Thus, it is possible to define an odor vector representing the motion of the measurement point from the origin. The direction of the odor vector varies when the quality of the odor changes. This means that, if two odor vectors have the same direction, their quality is also the same, and the length of each odor vector, which is a scalar value, indicates the intensity of each odor. According to the present invention, the concentrations of n types of known standard odors are measured beforehand at plural concentration levels. This measurement gives n pieces of reference odor vectors created within the m-dimensional space, and they are used as the reference axes for evaluating the quality and strength of unknown odors. In the case the moving direction of the measurement point within the m-dimensional space according to the change of the concentration of the standard odor has no relevance, it is allowable to create a simple curve showing the locus of the measurement points, instead of drawing a vector. The n pieces of reference odor curves are then used as the reference axes instead of the n pieces of standard odor vectors.

Thus, when the m pieces of the odor sensors generate detection outputs at a certain point in time, the calculator locates a measurement point that represents the outputs within the m-dimensional space and calculates an index representing the similarity between the component detected at the aforementioned point in time and the standard odors and/or an index representing the degree of intensity of the unknown odor on the basis of the positional relation of the measurement point to the n pieces of the reference axes. For example, the similarity between the component and each standard odor is calculated from the spatial distance (or closeness) between the measurement point and each reference axis. Furthermore, the odor concentration is calculated by a process including the steps of locating the projection point of the measurement point on each reference axis (excluding those axes for which the similarity is zero), calculating the substance concentration corresponding to the projection point, and dividing the substance concentration by the odor threshold value for the standard odor concerned. Then, the odor concentration is logarithmically transformed to obtain an analogue value of the odor index. When the type of the sample component introduced into the detector changes with the lapse of time, the outputs of the odor sensors accordingly change. Taking this into account, the information creator repeats the above-described process to create a set of information that shows the change of the index with the lapse of time.

In general, the response speed of an odor sensor is not very high. As a result, the odor sensor often fails to generate an adequately distinct output for each sample component if the temporal intervals of two or more components separated by the chromatograph are very small or the sample contains a considerable amount of contaminants. Taking this into account, if the response speed of the odor sensors is low, it is preferable that the component separator is a two-dimensional gas chromatograph with a series of two separation columns having different levels of selectivity, which selects necessary components contained in the target gas and send the selected component to the detector.

In the two-dimensional gas chromatograph, the first separation column temporally separates the sample components, and a heart-cut valve or similar device removes contaminants or other unnecessary components from the effluent gas coming from the first column. Next, the second separation column provides a clearer separation of the target components and introduces the components into the detector. This ensures an adequately long time between the introduction of one sample component into the detector and the introduction of another sample component into the detector. Therefore, even if the response speed of the odor sensors is low, the apparatus can clearly detect the target component of the sample and calculate the aforementioned index without being influenced by other components.

In a form of the odor measuring apparatus according to the present invention, the component separator is a gas chromatograph having a separation column, and the apparatus further includes:

a splitter for splitting a flow of the gas sample from the separation column into at least two branches; and a mass analyzer for carrying out the mass analysis of the first branch of the gas sample, and the second branch of the gas sample is introduced into the detector. The use of the mass analyzer enables the creation of a mass spectrum at each point in time and/or a mass chromatogram focusing on a specific mass number in parallel with the odor measurement. The data obtained hereby may be related with the aforementioned information about the temporal change of the quality and/or intensity of the odor and presented to the user.

The odor measuring apparatus according to the present invention can separate even a complexly mixed odor into sample components and calculate an objective index indicating the quality and/or intensity of the odor of each component. The index can be transformed to an odor index that reflects the characteristics of the olfactory sense of the human being. The apparatus can separate and detect even a very small quantity of a component accompanied by a very large quantity of another component. Thus, the quality and intensity of an odor component that could not have been detected by conventional methods can now be objectively presented.

DETAILED DESCRIPTION OF A PREFERRED EMBODIMENT

Figure 1:
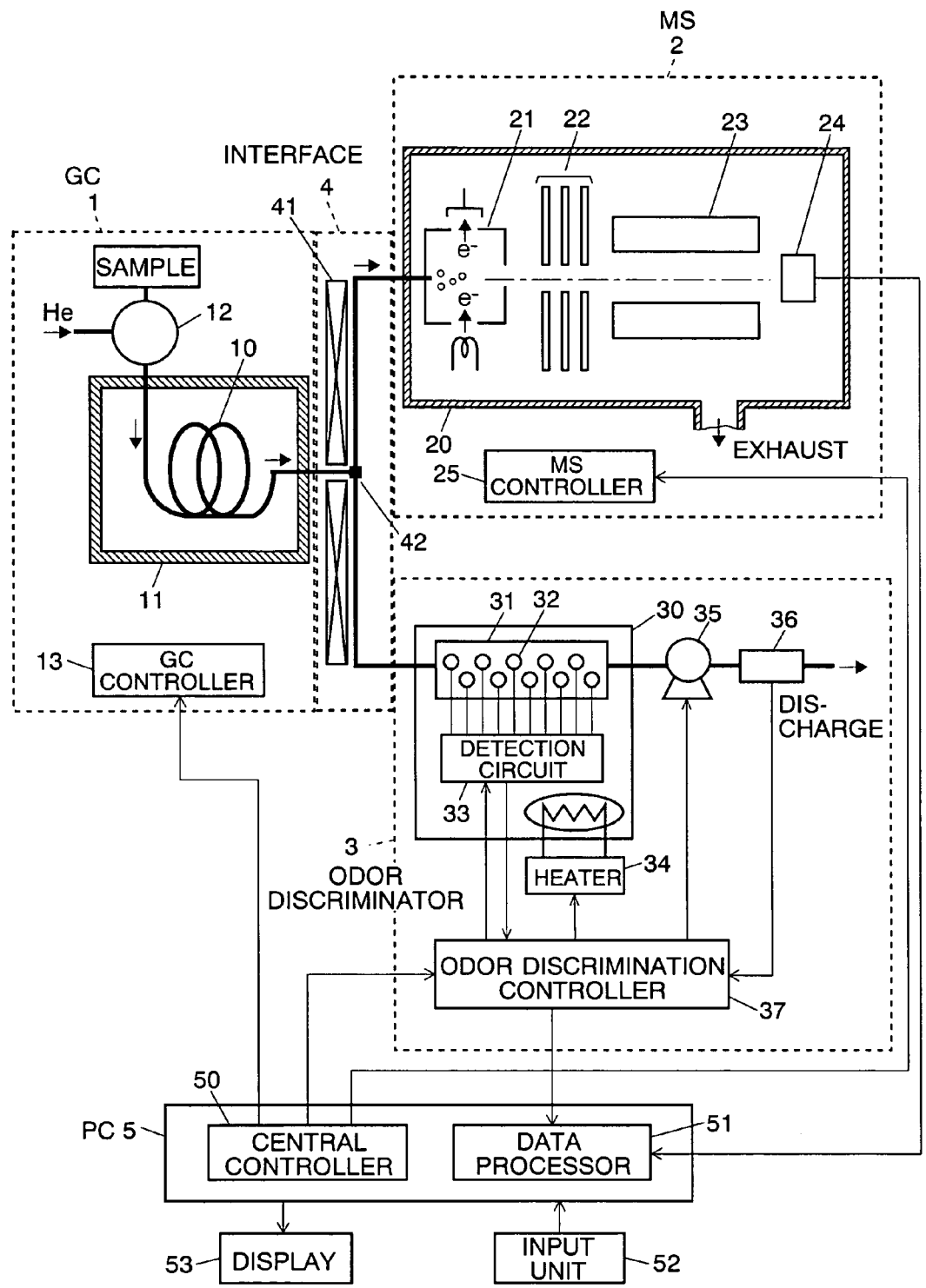
FIG. 1 is a block diagram showing an odor measuring apparatus as an embodiment of the present invention.

An odor measuring apparatus as an embodiment of the present invention is described with reference to the attached drawings. FIG. 1 is a block diagram showing the odor measuring apparatus in this embodiment.

The odor measuring apparatus is mainly composed of a gas chromatograph (GC) 1, a mass spectrometer (MS) 2, an odor discriminator 3, and an interface 4. The GC 1 includes a separation column 10 enclosed in a column oven 11, a sample injector 12 located at the inlet of the column 10, and a GC controller 13 for controlling the aforementioned elements of the GC 1. The MS 2 includes a vacuum chamber 20, an ion source 21 for ionizing molecules of the components contained in the introduced gas sample, an ion optics 22 for conveying the generated ions, a quadrupole mass filter 23 for separating the ions with respect to their mass numbers, an ion detector 24 for detecting the separated ions, and an MS controller 25 for controlling the aforementioned elements of the MS 2.

The odor discriminator 3 includes a thermostatic chamber 30, a sensor cell 31 with ten pieces of odor sensors 32 having different response characteristics, a detection circuit 33 for detecting the varying output of each odor sensor, a heater 34 for maintaining the temperature of the thermostatic chamber 30, a pump 35 for drawing the gas sample into the sensor cell 31, a flow sensor 36 for measuring the flow rate of the gas, and an odor discrimination controller 37 for controlling the aforementioned elements of the odor discriminator 3. It should be noted that the number of odor sensors 32 used in the sensor cell 31, which is ten in this embodiment, may be different. The interface 4, which is located between GC 1 and MS 2 and also between GC 1 and odor discriminator 3, includes a heater 41 for maintaining the pipeline at a high temperature to ensure a smooth flow of the gas sample, and a splitter 42 for splitting the gas sample into two branches. The odor measuring apparatus further includes a personal computer 5, which functions as a data processor 51 for analyzing signals generated by the detection circuit 33 of the odor discriminator 3 and a central processor 50 for generally controlling the aforementioned controllers 13, 25 and 37. The computer 5 is equipped with an input unit (e.g. a keyboard) 52 and a display 53.

The odor sensor 32, for example, is a sensor using metal oxide semiconductors whose resistance varies depending on the kinds of odor components. Alternatively, the odor sensor 32 may be a sensor using conductive high polymers, a sensor using quartz resonators or a SAW (surface acoustic wave) device coated with a gas absorption film.

In the odor measuring apparatus constructed as described above, the odor discriminator 3 detects and discriminates odors as described below.

As explained previously, the ten odor sensors 32 have different response characteristics. This enables the creation of a ten-dimensional space having ten pieces of independent axes corresponding to the outputs of the ten odor sensors 32. The origin of the ten-dimensional space is the point where the outputs of the odor sensors 32 are all zero, meaning that there is no odor detected. Upon detecting an odor, the ten odor sensors 32 generate outputs, which can be located as a measurement point within the ten-dimensional odor space. Starting from the odorless state, as the odor becomes more intense, the measurement point moves from the origin in a certain direction within the ten-dimensional space. For another odor having a different quality, the measurement point will move from the origin in a different direction. In summary:

(1) When a sample having a certain odor is measured, the ten odor sensors 32 will generate outputs that can be represented by a measurement point within the ten-dimensional space.
(2) When plural samples having different concentrations of the same odor are sequentially measured, the measurement point for the odor will move in a certain direction according to the change of the concentration.
(3) The plural measurement points will form a line represented by a vector extending from the origin. This is called the "odor vector" in this specification.

Figure 2:
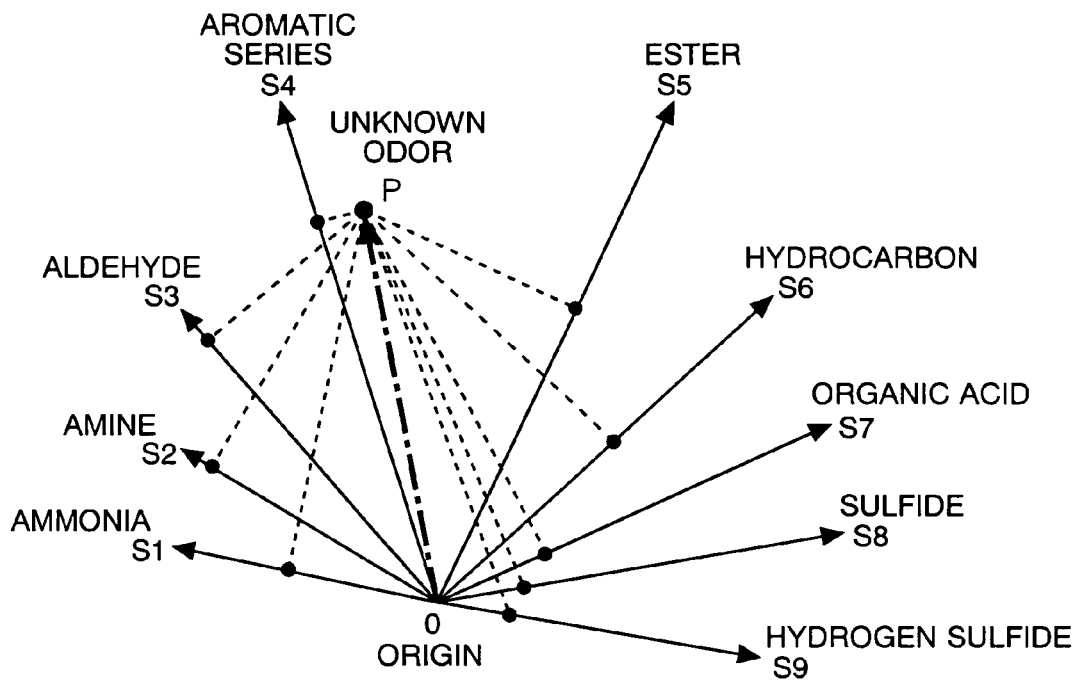
FIG. 2 illustrates the principle of the measurement carried out by the odor discriminator of the odor measuring apparatus shown in FIG. 1.

In the ten-dimensional space, the direction of the odor vector represents the odor quality, and the vector length from the origin represents the odor intensity. Taking this into account, plural types of standard odors, each odor having a known quality, are prepared beforehand, and plural samples of each standard odor having different odor concentrations are measured to obtain an odor vector for the standard odor. This is defined as the reference odor vector. The present embodiment uses the following nine types of standard odors: hydrogen sulfides, sulfur compounds (e.g. methyl mercaptan), organic acids (e.g. butyric acid), hydrocarbons, esters (e.g. acetic ester), aromatic series (e.g. toluene), aldehydes (e.g. butyraldehyde), amines (e.g. trimethylamine) and ammonia. FIG. 2 schematically shows the nine reference odor vectors S1–S9 corresponding to the nine standard odors within the ten-dimensional space. Regarding the nine reference odor vectors S1–S9 as the reference axes, the data that define the nine odor vectors S1–S9 are stored in a memory or other storage device as the reference data.

When an unknown odor is measured, the measurement result can be located as a measurement point P within the ten-dimensional odor space in which the aforementioned reference odor vectors are created. If the unknown odor is one of the standard odors, the measurement point must ideally be located on the reference odor vector corresponding to the standard odor concerned. This suggests that the distance (or closeness) between the measurement point and each reference odor vector provides a basis for determining the similarity between the unknown odor and each standard odor. The degree of distance (or closeness) between the measurement point and each reference odor vector can be determined by various methods. For example, the angle between the vector extending from the origin to the measurement point P and each of the nine reference odor vectors S1–S9 may be used to calculate the similarity in odor quality. It is also possible to calculate the minimal distance between the measurement point P and each of the reference odor vectors S1–S9 and determine the similarity from the minimal distance. In a preferable example, the index that shows the similarity (or difference) in odor quality indicates the degree of distance (or closeness) between the unknown odor and each standard odor by a value between 100% (if the odor quality is completely identical) and 0% (if the odor quality is completely different).

The odor intensity can be represented by the degree of contribution of the analogue value of the odor index of each standard odor. The analogue value of the odor index of a standard odor is calculated as follows. Given an unknown odor, an orthogonal projection of the unknown odor vector is created onto the reference odor vector corresponding to the standard odor vector concerned. Each position on the reference odor vector corresponds to a certain substance concentration of the standard odor. Therefore, the projected length of the unknown vector indicates the substance concentration of the standard odor contained in the unknown odor. Then, the substance concentration is divided by the odor threshold value (i.e. the minimum concentration that the human nose can sense) for the standard odor to obtain an odor concentration. Finally the odor concentration is logarithmically transformed to obtain an analogue value of the odor index. The degree of contribution of the analogue value of the odor index is referred to as the "odor contribution" hereinafter.

Figure 3:
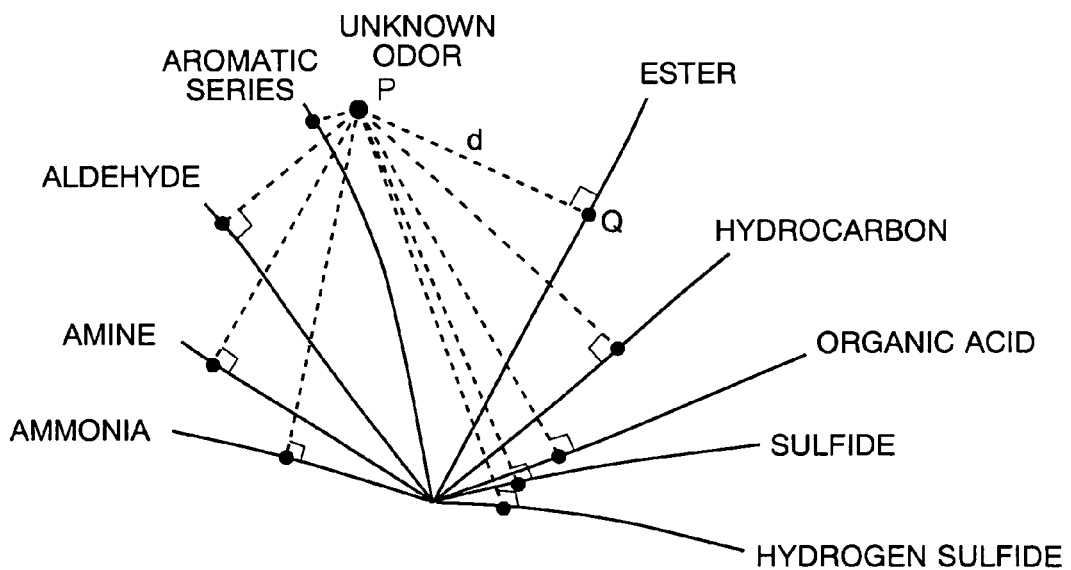
FIG. 3 illustrates the principle of the measurement carried out by the odor discriminator of the odor measuring apparatus shown in FIG. 1.

As described previously, the odor vector indicates the moving direction of the measurement point within the ten-dimensional space according to the change of the concentration (or the increase in the concentration). If the moving direction has no relevance, the odor vector can be replaced by a simple odor curve, and reference odor curves can be used instead of the reference odor vectors. As shown in FIG. 3, each reference odor curve is created from plural measurement points representing the varying outputs generated by the odor sensors 32 as the concentration of each standard odor component is varied. The reference odor curves are hereby used as the reference axes, and the data representing the reference odor curves are stored in a memory as the reference data. When an unknown odor is measured, the minimal distance from the measurement point P to each reference odor curve is calculated, and the similarity between the unknown odor and each standard odor is calculated from the minimal distance. Furthermore, the analogue value of the odor index of the standard odor is calculated from the concentration corresponding to the point Q that gives the minimal distance on the reference odor curve.

The method of calculating the index indicating the similarity in odor quality, and the method of calculating the odor concentration or the analogue value of the odor index, both indicating the odor intensity, are not restricted to the above-described ones. For example, the methods disclosed in the Japanese Unexamined Patent Publication No. 2003-315298 are all applicable to this embodiment.

The overall operation of the odor measuring apparatus in this embodiment is described. The gas sample to be measured is contained in a sample bag attached to the sample injection port 12. Being controlled by the GC controller 13, a carrier gas pushes the gas sample to send it through the sample injection port 12 into the column 10 according to a predetermined time schedule. The gas sample is separated into different kinds of odor components while it is passing through the column 10. The odor components exit the column 10 at different points in time. In the interface 4, the odor components are split into two branches: one leading to the MS 2 and the other leading to the odor discriminator 3. In MS 2, the ionizer 21 sequentially ionizes the odor components, and the quadrupole mass filter 23 selects only such ions that have a specific mass number. The ions thus selected reach the ion detector 24. Being controlled by the MS controller 25, the quadrupole mass filter 23 repeatedly scans a predetermined mass range. For every scan of the mass range, the ion detector 24 generates detection signals, from which a mass spectrum is created. The data processor 51 processes the detection signals of the ion detector 24 to repeatedly create a series of mass spectrums in which the abscissa indicates mass number and the ordinate indicates signal intensity. It is also possible to create a total ion chromatogram in which the abscissa indicates time and the ordinate indicates signal intensity, without considering the mass number. Focusing on a specific mass number provides a mass chromatogram in which the abscissa indicates time and the ordinate indicates signal intensity.

In the odor discriminator 3, the odor discrimination controller 37 controls the pump 35 to introduce the gas sample into the sensor cell 31 so that the flow rate detected by the flow sensor 36 is maintained at a predetermined level. When the odor components contained in the gas sample come in contact with the odor sensors 32, the odor sensors 32 and the detection circuit 33 generate a set of detection signals. Since the plural odor components are temporally separated by the GC 1, the odor discriminator 3 separately generates a set of detection signals for each odor component. The data processor 51 collects the detection signals at predetermined intervals of time. Alternatively, the timing for collecting the signals may be determined from the result of the detection of the ions by the MS 2. This method will be described later.

Figure 4:
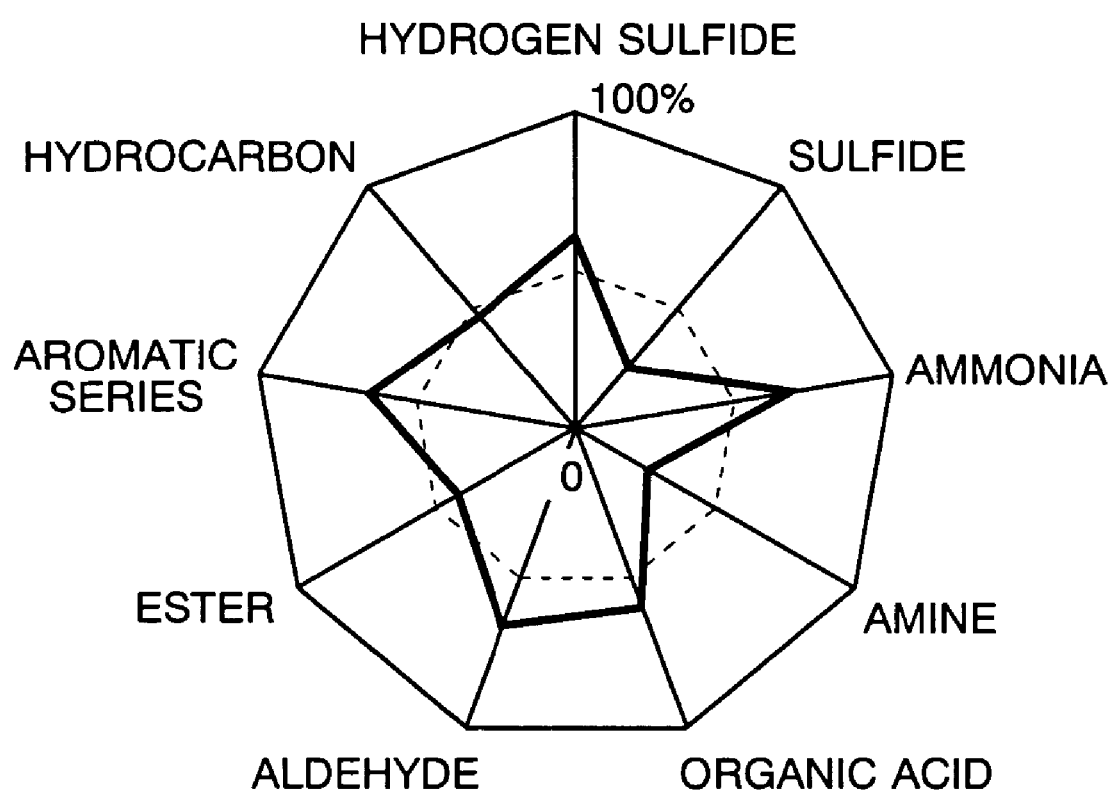
FIG. 4 shows an example of the result of the measurement carried out by the odor discriminator of the odor measuring apparatus shown in FIG. 1.

Based on the detection signals received from the odor discriminator 3, the data processor 51 carries out the data processing using the reference data, as described previously, to calculate the similarity, the analogue value of the odor index and/or other values for each odor component. In the case the detection signals are collected at predetermined intervals of time, the similarity and other values of each odor component are calculated for every interval of time, and an odor chromatogram is created, in which the abscissa indicates time and the ordinate indicates the total odor index or the similarity or odor contribution of a certain standard odor (e.g. sulfur compound or amine). The odor chromatogram is presented on the display 53. It is also possible to relate the measurement result obtained by the odor discriminator 3 to that obtained by MS 2, and simultaneously show the two results on the display 53. For example, the information displayed may include a total ion chromatogram having one or more peaks, where each peak is associated with a radar chart showing the similarities of the unknown odor to the standard odors (FIG. 4) and/or a radar chart showing the odor contributions of the standard odors to the unknown odor at the point in time at which the peak is located.

The odor measuring apparatus according to this embodiment calculates the similarity and the odor contribution of an unknown odor primarily on the basis of reference data relating to the predetermined nine types of standard odors, as described previously. In addition, the user is allowed to use an additional standard odor, e.g. a gasified odor that is closely related to the unknown odor to be measured. In this case, the user should create an additional reference axis that corresponds to the additional standard odor. The additional reference axis enables the calculation of the similarity between the unknown odor and the additional standard odor. However, it is impossible to calculate the odor contribution of the additional standard odor because there is no information about the relation between each point on the additional reference axis and the concentration of the component contained in the gasified odor.

In practice, users desire to view the aforementioned radar charts mainly at a point or points on the chromatogram where a peak or peaks are located, i.e. where some odor is detected. Taking this into account, it is possible to collect the detection signals of the odor sensors 32 at each point in time where a peak top is located on the chromatogram created in real-time from the detection result of the MS 2. For this purpose, it is preferable to determine the lengths of the passage in the interface 4 so that the detection of the odor component in the MS 2 is synchronized with that in the odor discriminator 3. If the detection data obtained with the odor sensors 32 are collected only at each point where a peak is located, the frequency of the data collection becomes lower. This is desirable when odor sensors whose response speed is relatively low are used.

In general, the response speed of an odor sensor is considerably lower than that of the detector typically used in a chromatograph. Therefore, if there are two different odor components located close to each other in the effluent gas, it is possible that the odor sensors cannot detect them as separate components while the detector of the chromatograph can detect them. This problem can be solved by using a two-dimensional chromatograph as the GC 1. In the two-dimensional chromatograph, two columns having different polarities are connected in series via a switching valve or similar device. The first column performs the initial, rough separation of the components contained in the sample. The selector valve performs the "heart-cut" operation; it removes unnecessary components while leaving necessary components. The second column receives only the necessary components and separates them more clearly. This ensures an adequately long interval of time between the two components, so that even an odor sensor having a low response speed can precisely detect them.

In the above-described embodiment, the odor components separated by the GC 1 are introduced into the MS 2 and the odor discriminator 3 in parallel. It is also possible to introduce a part of the odor components into an additional olfactory detector for an evaluator to directly smell the odor and enter the odor intensity or other information. It should be noted that the embodiment may be further modified or extended in other aspects within the spirit and scope of the present invention.

What is claimed is:

1. An odor measuring apparatus for analyzing a target gas having an odor, comprising:
   a) a component separator for temporally separating the target gas into sample components;
   b) a detector having m pieces of odor sensors for sequentially detecting the separated sample components with a lapse of time, where m is an integer greater than one and the odor sensors have different response characteristics;
   c) a reference data storage for storing data representing n pieces of reference odor vectors or reference odor curves defined by results of the measurements of n types of known standard odors within an m-dimensional space formed by detection signals of the m pieces of the odor sensors;
   d) a calculator for locating, within the m-dimensional space, a measurement point representing the detection outputs generated by the m pieces of the odor sensors at a certain point in time, and for calculating an index indicating a similarity between the sample component detected at the aforementioned point in time and the standard odors and/or an index representing a degree of intensity of an unknown odor on a basis of a positional relation of the measurement point to the n pieces of the reference odor vectors or the reference odor curves stored in the reference data storage; and
   e) an information creator for creating a piece of information showing a change of the index with a lapse of time.

2. The odor measuring apparatus according to claim 1, wherein the component separator is a gas chromatograph having a separation column, and the apparatus further comprises:
   a splitter for splitting a flow of the target gas from the separation column into at least two branches; and
   a mass analyzer for carrying out a mass analysis of the first branch of the target gas, and the second branch of the target gas is introduced into the detector.

3. The odor measuring apparatus according to claim 1, wherein the component separator is a two-dimensional gas chromatograph with a series of two separation columns having different levels of selectivity, which selects necessary components contained in the target gas and send the selected component to the detector.

4. The odor measuring apparatus according to claim 3, wherein the component separator comprises a heart-cut valve for removing contaminants or other unnecessary components from an effluent gas coming from the first column.

5. The odor measuring apparatus according to claim 1, wherein the calculator calculates the similarity between the sample component and each standard odor from a spatial distance or closeness between the measurement point and the reference odor vector or the reference odor curve corresponding the standard odor concerned.

6. The odor measuring apparatus according to claim 1, wherein the calculator calculates an odor concentration by a process including the steps of locating a projection point of the measurement point on each reference axis, calculating a substance concentration corresponding to the projection point, and dividing the substance concentration by an odor threshold value for the standard odor concerned.

* * * * *